(12) United States Patent
Pathak

(10) Patent No.: US 7,476,246 B2
(45) Date of Patent: Jan. 13, 2009

(54) IMPLANTABLE MEDICAL DEVICES WITH FLUORINATED POLYMER COATINGS, AND METHODS OF COATING THEREOF

(75) Inventor: Chandrashekhar Prabhakar Pathak, Phoenix, AZ (US)

(73) Assignee: C. R. Bard, Inc., Murry Hill, NJ (US)

( * ) Notice: Subject to any disclaimer, the term of this patent is extended or adjusted under 35 U.S.C. 154(b) by 555 days.

(21) Appl. No.: 11/006,946

(22) Filed: Dec. 7, 2004

(65) Prior Publication Data

US 2005/0131527 A1    Jun. 16, 2005

Related U.S. Application Data

(60) Provisional application No. 60/549,770, filed on Mar. 3, 2004, provisional application No. 60/529,402, filed on Dec. 12, 2003.

(51) Int. Cl.
*A61F 2/06* (2006.01)
(52) U.S. Cl. .................. 623/1.46; 427/2.1
(58) Field of Classification Search ....... 623/1.11–1.48; 427/2.1
See application file for complete search history.

(56) References Cited

U.S. PATENT DOCUMENTS

| | | | |
|---|---|---|---|
| 3,922,378 A | | 11/1975 | Kline |
| 5,116,650 A | * | 5/1992 | Bowser ................. 428/34.2 |
| 5,238,471 A | * | 8/1993 | Blanchet-Fincher ........... 96/13 |
| 6,753,071 B1 | * | 6/2004 | Pacetti ................. 428/212 |
| 6,770,202 B1 | * | 8/2004 | Kidd et al. ............... 210/650 |
| 6,884,375 B2 | * | 4/2005 | Wang et al. ................. 264/41 |
| 7,056,550 B2 | * | 6/2006 | Davila et al. ............. 427/2.24 |
| 7,166,570 B2 | * | 1/2007 | Hunter et al. ................. 514/2 |
| 2001/0049551 A1 | | 12/2001 | Tseng et al. |
| 2004/0220665 A1 | * | 11/2004 | Hossainy et al. .......... 623/1.42 |

FOREIGN PATENT DOCUMENTS

| | | |
|---|---|---|
| EP | 0 775 472 A2 | 5/1997 |
| EP | 0797963 A2 | 10/1997 |
| WO | WO 95/05132 | 2/1995 |
| WO | WO 00/56247 | 9/2000 |
| WO | WO2004/026359 | 4/2004 |

OTHER PUBLICATIONS

Cameron Haery, M.D. et al., Drug-eluting stents: The beginning of the end of restenosis?, Cleveland Clinic Journal of Medicine, vol. 71, No. 10, pp. 815-824, Oct. 2004.

* cited by examiner

*Primary Examiner*—Suzette J Gherbi

(57) ABSTRACT

The present invention generally relates to implantable medical devices having a fluorinated coating, and methods of coating the same. More particularly, the present invention provides implantable metallic medical devices coated with a corrosion resistant coating comprising an amorphous fluoropolymer.

26 Claims, No Drawings

IMPLANTABLE MEDICAL DEVICES WITH FLUORINATED POLYMER COATINGS, AND METHODS OF COATING THEREOF

CROSS-REFERENCE TO RELATED APPLICATION

This application claims the benefit of priority of U.S. Provisional Application No. 60/549,770, filed Mar. 3, 2004, and of U.S. Provisional Application No. 60/529,402, filed Dec. 12, 2003.

BACKGROUND OF THE INVENTION

Implantable stents and other expandable medical devices have been increasingly used in many minimally invasive surgical procedures such as balloon angioplasty. Stents mitigate complications of acute and subacute vessel closure, intimal dissection, and elastic recoil of the vessel wall, and reduce angioplasty-related restenosis rates. Restenosis can be caused by incompatibility of the metallic surface of the stent that engages the inner walls of the blood vessel, giving rise to subacute thrombosis. Another possible cause of restenosis is the recoil of the metallic surface of the stent when placed along the internal wall of the artery. In-stent restenosis usually occurs within weeks to months of stent implantation.

Some metallic devices such as vascular stents, made from stainless steel or Nitinol alloys (Shape Memory Alloys, such as Nickel Titanium alloy), may undergo corrosion upon long-term implantation. The corrosion products such as transition metal ions may be toxic to the surrounding tissue. To prevent corrosion, stents or stent-grafts have been coated with a polymeric or biological material. However, when coated stents are expanded within a blood vessel, the coefficient of expansion of the coating greatly differs from that of the expanding stent such that, upon expansion, the surface of the coating tears rendering the expanded stent uncoated. If a thicker coating is applied, such a thick coating can deter stent expansion or can render implantation into the body difficult. Thus, challenges remain in developing biostable metallic implantable devices.

BRIEF SUMMARY OF THE INVENTION

The present invention generally relates to implantable medical devices having a fluorinated coating, and methods of coating the same. More particularly, the present invention provides implantable metallic medical devices coated with a corrosion resistant coating comprising an amorphous fluoropolymer. The present invention also provides methods for depositing a thin layer of fluorinated polymeric coating on such medical devices. Examples of implantable medical devices that may be coated using the present methods include but are not limited to angioplasty balloons, catheters, guide wires, vascular patches, filters, vascular stents, drug-eluting stents for use in controlled drug delivery, and other expandable medical devices.

In one aspect, the present invention provides a vascular stent having a metal surface coated with an amorphous fluoropolymer coating comprising tetrafluoroethylene (TEF) and 4,5-difluoro-2,2-bis(trifluoromethyl)-1,3-dioxole, or a perfluoroelastomer, wherein the coating has a thickness from 1 to 100 microns. The present invention also provides methods for coating a vascular stent, comprising contacting a metal surface of a vascular stent with a solution comprising an amorphous fluoropolymer and a fluorinated organic solvent to provide a coating having a thickness from 1 to 100 microns, wherein the amorphous fluoropolymer comprises tetrafluoroethylene (TEF) and 4,5-difluoro-2,2-bis(trifluoromethyl)-1,3-dioxole, or a perfluoroelastomer.

The metal surface of the stent may be made of stainless steel, titanium, nickel, a metal alloy, platinum, gold, or a biocompatible metal. In particular examples, the metal may be made of a titanium and nickel alloy, or NITINOL®. As described in more detail below, the metal surface may be coated with an optically transparent, radioopaque, chemically resistant or porous amorphous fluoropolymer coating. The coating may have a thickness from 1 to 20 microns. In other examples, the coating has a thickness from 5 to 15 microns. Furthermore, the coating may have a low coefficient of friction (e.g., from 0.01 to 0.4).

The amorphous fluoropolymer coating solution may comprise tetrafluoroethylene (TEF) and from 60 mole % to 90 mole % of 4,5-difluoro-2,2-bis(trifluoromethyl)-1,3-dioxole. Examples of amorphous fluoropolymer coatings include but are not limited to TEFLON AF 1600®, TEFLON AF 2400®, or CHEMRAZ® or KALREZ® perfluoroelastomer. In one example, the solution comprises from 0.1% to 30% by weight of the amorphous fluoropolymer. In other examples, the solution comprises from 1% to 10% by weight of the amorphous fluoropolymer. In yet other examples, the solution comprises 5% by weight of the amorphous fluoropolymer, which may further comprise 5% by weight of a therapeutic agent.

The surface of the stent may be contacted with a homogenous solution comprising an amorphous fluoropolymer and a fluorinated organic solvent, such as FLUORINERT®. The solution may further be filtered prior to contacting to the metal surface of the stent. The stent may also be coated by dipping or spraying the stent with the solution comprising the amorphous fluoropolymer and the fluorinated organic solvent, which may further be dried.

In one embodiment, the vascular stents may be capable of releasing a therapeutic agent. For example, the stent may be contacted with a coating solution comprising a therapeutic agent. Examples of therapeutic agents that may be released from stents include but are not limited to an anti-restenotic agent, an anti-stenotic agent, an antiproliferative agent, an immunomodulator, an antithrombotic, an antioxidant, estrogen, a growth factor inhibitor, an antisense oligonucleotide, or a collagen inhibitor. In one example, the therapeutic agent is paclitaxel.

In another embodiment, the vascular stent is radioopaque. For example, the stent is contacted with a solution modified by addition of a radioopaque agent to provide a stent having a first coating, which is further contacted with a solution having no radioopaque agent. Examples of radioopaque agents include but are not limited to barium sulfate, gold, tantalum, triiodobenzoic acid, or a triiodobenzoic acid derivative.

In another example, the vascular stent is coated with a porous fluoropolymer coating. For example, the metal surface of the stent is contacted with a solution modified by addition of a salt or a compound capable of releasing a gas to provide a coated stent, which is further contacted in an aqueous medium to obtain a porous amorphous fluoropolymer coating. The salt may be an alkali metal salt, an alkaline metal salt, or any inorganic salt that may be used for controlling the porosity of the fluoropolymer coating. The compound in the modified solution may be capable of releasing carbon dioxide upon decomposition, such as an isocyanate moiety.

These and other embodiments, features and advantages of the present invention will become more apparent to those skilled in the art when taken with reference to the following more detailed description of the invention.

DETAILED DESCRIPTION OF THE INVENTION

The present invention provides metallic implantable medical devices having an amorphous fluorinated coating, and methods of coating thereof. In particular examples, the amorphous fluorinated coating is optically transparent and resistant to chemical corrosion.

Polytetrafluoroethylene (PTFE) with its low surface tension, low coefficient of friction, excellent chemical and thermal stability combined with excellent dielectric properties, have favored its application in various medical devices. However, because PTFE is insoluble in commonly used organic solvents, the possibilities for processing PTFE are limited to the aqueous dispersion or to its granular form with high melt-viscosity. Thus, it is also difficult to obtain a thin coating with PTFE using conventional PTFE manufacturing processes such as spray or dip coating methods. These unattractive features have challenged further research, striving for materials with comparable properties but more flexible processing.

A variety of comonomers have been introduced in the PTFE chains to obtain copolymers of lower molar mass and reduced melt-viscosity, while maintaining adequate mechanical and physical properties. Examples of such copolymers are those comprising hexafluoropropylene (FEP) and perfluoroalkyl-vinyl-ethers (PFAs), or perfluoro-(2,2-dimethyl-1,3-dioxole) (Teflon AF). Fluorinated polymers such as Poly[4,5-difluoro-2,2-bis(trifluoromethyl)-1,3-dioxole-co-tetrafluoroethylene],65 mole % dioxole (Teflon® AF 1600) and Poly[4,5-difluoro-2,2-bis(trifluoromethyl)-1,3-dioxole-co-tetrafluoroethylene], 87 mole % dioxole (Teflon® AF 2400) have recently become commercially available.

The molecular structure of Poly[4,5-difluoro-2,2-bis(trifluoromethyl)-1,3-dioxole-co-tetrafluoroethylene] is given below:

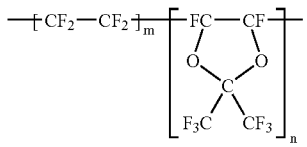

where m and n are integers or other numbers representing the degree of polymerization, and of the proportions of the different monomeric units incorporated in the polymer. The presence of 4,5-difluoro-2,2-bis(trifluoromethyl)-1,3-dioxole moiety in PTFE chain prevents crystallization of the polymeric chain, and allows the formation of substantially amorphous polymers. The amorphous nature of the polymer permits limited solubility in certain fluorinated solvent/solvent mixtures at room temperature. The amorphous nature of the polymer also gives optically transparent films.

The physical properties of TEFLON® AF are similar to the PTFE homopolymer. However, TEFLON® AF 2400 is soluble in fluorinated organic solvents including but not limited to FLUORINERT® FC75, FLUORINERT® FC40, FLUORINERT®FC72, perfluoro (PF) methyl cyclohexane, PF benzene, PF octane, PF dimethyl cyclohexane, PF decalin, PF 1-methyldecalin, PF dimethyldecalin. Thus, the fluorinated backbone of TEFLON® AF should provide similar biocompatibility and biostability as the PTFE homopolymer. In general, an increased amount of 4,5-difluoro-2,2-bis(trifluoromethyl)-1,3-dioxole in the copolymer, results in an increased melting point and decreased solubility in fluorinated solvents. In particular examples, a copolymer with 60-90% of 4,5-difluoro-2,2-bis(trifluoromethyl)-1,3-dioxole content is used in coating a metallic implantable medical device.

In one embodiment, the present invention provides an implantable medical device made of Nitinol (nickel titanium alloy) having an amorphous fluoropolymer coating. Nitinol-based vascular grafts and stents are typically deployed using minimally invasive balloon angioplasty techniques. Briefly, a compressed Nitinol stent is mounted on a catheter delivery system and is maintained in the compressed state by covering the stent with a removable sleeve. Upon transporting the stent to the site of implantation, the protective sleeve is removed and the stent self expands to a predetermined geometrical shape (a property of Nitinol alloy). To permit easier sleeve removal, a stent surface with low coefficient of friction is desired. Therefore, it would also be advantageous to provide coating methods and compositions that provide low friction properties.

In a particular example, a 5% solution of Poly[4,5-difluoro-2,2-bis(trifluoromethyl)-1,3-dioxole-co-tetrafluoroethylene] in FC 75 is spray coated on a Nitinol based vascular stent (expanded prior to coating). Upon complete evaporation of solvent, the stent is compressed, mounted on a catheter and re-expanded to its original expanded shape. The coating survives compression and expansion of stent without substantial damage. The coating is chemically stable when exposed to various acidic, basic and oxidizing chemicals typically found in the human or animal body. The coating is also optically transparent to visible light indicating the amorphous nature of the polymer.

Various techniques known in the art for improving coating adhesion may be used in the present methods. For example, prior to spray coating, the stent surface may be cleaned with a cleaning agent such as isopropanol to improve adhesion of the coating to the substrate. Other adhesion treatments such as plasma etching, chemical etching, treatment with perfluorodecyltriethoxy silane and the like may also be used to improve adhesion of Teflon AF to the stent surface.

Coating thickness may be controlled by controlling polymer concentration in the solvent and spray coating parameters. The polymer concentration in the solvent may be from 0.1% to 30%, or from 1 to 10% percent. The coating thickness may be from 1 to 100 microns, or from 1 to 20 microns. In other examples, the coating thickness may be from 5 to 15 microns. If desired, multiple coats may be applied to achieve a desired thickness.

Furthermore, the coating may have a low coefficient of friction similar to PTFE. As used herein, the term "coefficient of friction" refers to the measure of the sliding resistance of a material over another material. For example, the coating may have a coating between 0.01 and 0.4.

In one embodiment, the amorphous fluoropolymer further may comprise a radioopaque agent. Many medical devices such as vascular stents and stent-grafts are designed to be radiopaque. The radiopacity permits easier visualization and therefore transportation to the site of implantation. Therefore, it would also be advantageous to provide fluorocarbon based radiopaque compositions and methods.

For example, a radiopaque agent such as iodinated compound is added in the polymer coating solution. The solution is spray coated to obtain a film having a thickness from 1 to 30 microns. If desired, another coat is provided on top of the radiopaque coat to prevent the leaching of the radiopaque compound into the surrounding tissue. The radiopaque agent that can be coated or encapsulated in amorphous polytetrafluoroethylene polymer includes, but is not limited to, barium sulfate, metal powders such as gold or tantalum powder, iodinated compounds such as triiodobenzoic acid, triiodobenzoic acid derivatives like Iohexol and the like. In particular examples, organic compounds such as iodinated compounds are used because they can be dissolved along with the polymer and form a homogeneous solution.

In another embodiment, the amorphous fluoropolymer may further comprise a therapeutic agent. Examples of therapeutic agents for use in the present invention include, but are not limited to, an anti-restenotic agent, an anti-stenotic agent, an antiproliferative agent, an immunomodulator, an antithrombotic, an antioxidant, estrogen, a growth factor inhibitor, an antisense oligonucleotide, or a collagen inhibitor. Examples of antiproliferative agents include, but are not limited to, sirolimus, paclitaxel and other taxanes, tacrolimus, everolimus, vincristine, vinblastine, HMG-CoA reductase inhibitors, doxorubicin, colchicines, actinomycin D, mitomycin C, cyclosporine, mycophenolic acid, and other known antiproliferative agents. Examples of immunomodulators include, but are not limited to, dexamethasone, methylprednisolone, gamma interfererons, and other known immunomodulators. Examples of antithrombotics include, but are not limited to, heparin, abciximab, and other known antithrombotics. Examples of antioxidants and estrogen include, but are not limited to, probucol and 17-beta estradiol, respectively. Examples of growth factor inhibitors include, but are not limited to, tranilast, tradipil, angiopeptin, and other known growth factor inhibitors. Examples of antisense oligonucleotides include, but are not limited to, to c-myc, c-myb and other known antisense oligonucleotides. Examples of collagen inhibitors include, but are not limited to, halofuginone, batimistat, and other known collagen inhibitors.

In one example, paclitaxel, an anti-restenotic agent, is dissolved along with Poly[4,5-difluoro-2,2-bis(trifluoromethyl)-1,3-dioxole-co-tetrafluoroethylene] in CF 75 (polymer concentration 5% and paclitaxel concentration 5%). A stainless steel coronary stent is first expanded, dipped in the paclitaxel solution and removed. The solvent is removed by air-drying and finally in vacuum at 40° C. for 24 hours. Additional dipping and evaporation steps may be performed until the desired coating thickness is achieved. The paclitaxel coated stent is then mounted on the angioplasty balloon catheter system and sterilized using ethylene oxide.

In yet another embodiment, the amorphous fluoropolymer coating is porous. Useful materials for medical devices such as vascular grafts and patches include but are not limited to generally porous PTFE or expanded PTFE (ePTFE), which promotes tissue in-growth due to its porosity. In the prior art, stretching a PTFE film or sheet and aligning the polymer chains along the direction of force is used to generate porosity. However, this method of generating porosity may not produce interconnected porous structures thought to promote tissue in-growth, which is a highly useful feature of many devices. Thus, it would also be advantageous to provide new fluorocarbon based compositions and methods for producing interconnected porous structures.

In one example, a porous amorphous fluorocarbon film is obtained by coating a suspension of water soluble salt such as sodium chloride along with Poly[4,5-difluoro-2,2-bis(trifluoromethyl)-1,3-dioxole-co-tetrafluoroethylene] dissolved in FC 40, and leaching the salt from the polymer to generate a porous structure in the polymer. The porosity can be controlled by the amount of salt added in the polymer solution and particle size of inorganic salt used. In another embodiment, porosity may be generated from compounds that release gas upon heating or upon a chemical or photochemical reaction. For example, an isocyanate compound like lysine diisocyanate may be added during a polymer solution preparation. Upon solvent removal, the coating is exposed to water where isocyanate decomposes and releases carbon dioxide, which creates porosity in the polymer. If the gas remains trapped inside the coating, the gas-filled coating may be useful in visualizing the device using standard ultrasonic medical imaging techniques.

The present methods may be practiced using various implantable medical devices, and with various methods of coating known in the art. (See e.g., WO 95/05132, WO 00/56247, U.S. Pat. Nos. 5,922,393, 5,891,507, 4,718,907, 6,488,701, EP patent 797 963, and EP 775 472, all of which are incorporated by reference herein). The present invention also contemplates the use of commercially available fluorinated elastomers, which are soluble in fluorinated solvents, as coatings for implantable medical devices. Examples of such fluorinated elastomers for use as coatings include but are not limited to CHEMRAZ® (a perfluoroelastomer from Greene, Tweed and Co Inc, Kulpsville Pa.) or KALREZ® (perfluoroelastomer from DuPont). Prior to use, these elastomers are cured or crosslinked to form a fluorinated elastomeric material.

Other amorphous fluoropolymer materials contemplated for use as coatings for implantable medical devices include amorphous fluoropolymer material coatings comprising random copolymers of tetrafluoroethylene (TEF) (also known as Teflon™.) and perfluoro-2,2-dimethyl-1,3-dioxole (PDD). Amorphous fluoropolymer materials may also comprise amorphous terpolymers of PDD and TEF, and another comonomer. The comonomer may comprise, but is not limited to, a perfluoroolefin or a perfluoro(alkyl vinyl ester). Other amorphous fluoropolymer coating materials may comprise dipolymers and terpolymers (collectively referred to as "copolymers") of PDD with comonomers, which may comprise perfluoroolefins and perfluoro(alkyl vinyl ethers).

It is further contemplated that the amorphous fluoropolymer materials for use as coatings for implantable medical devices may comprise amorphous homopolymers and copolymers which contain repeating cyclic structures formed during a cyclic polymerization of perfluoro(butenyl vinyl ether) (PBVE). These amorphous fluoropolymer materials exhibit enhanced mechanical and chemical stability when exposed to at least one of organic solvents and alkaline solutions.

Various methods known in the art for coating or depositing a thin film are also contemplated for use in practicing the present invention. For example, thin films may be deposited using vacuum pyrolysis. Nanometer size thin films may also be deposited using laser ablation, where a material is vaporized in a high vacuum environment by irradiation with a high power laser and the vapors are directed to the substrate for coating.

The following examples are intended to illustrate, but not to limit the present invention. Amorphous fluorinated polymers [(Poly[4,5-difluoro-2,2-bis(trifluoromethyl)-1,3-dioxole-co-tetrafluoroethylene] are purchased from Aldrich. These polymers also can be purchased from DuPont Inc. (Trade Name TEFLON® AF 1600, TEFLON® AF 2400). Fluorinated solvents such as FLUORINERT® FC75 and FC40 are purchased from Aldrich. Alternatively, FLUORINERT® solvents may be purchased from 3M Corporation.

EXAMPLE 1

Coating a Vascular Stent with Amorphous PTFE Polymer

In a 250 ml glass beaker, 1 g TEFLON® AF 1600 and 19 g FLUORINERT® FC40 are mixed until a homogeneous clear solution is obtained. The solution is filtered using a 0.2 micron glass filter, and then used in coating application. A Nitinol stent from Angiomed (Memoflexx stent 8 mm diameter, 50 mm length) is dipped in the polymer solution and removed from the solution. The solvent is removed by air-drying. A transparent thin polymer coating is visible on the stent surface when viewed microscope.

EXAMPLE 2

Method of Obtaining a Porous Fluoropolymer Coating

In a 250 ml glass beaker, 1 g TEFLON® AF 1600 and 19 g FLUORINERT® FC40 are mixed until a homogeneous clear solution is obtained. To this solution 5 g sodium chloride is added and the solution/suspension is stirred using a magnetic stirrer. A Nitinol stent from Angiomed (Memoflexx stent 8 mm diameter, 50 mm length) is dipped in the polymer solution. The solvent is removed by air-drying. The stent is then transferred into a beaker containing 1000 ml distilled water, and incubated until salt is leached out completely. The removal of salt creates a porous polymeric coating. The porosity may help to induce tissue in-growth.

The present invention has been described above in terms of certain preferred embodiments so that an understanding of the present invention can be conveyed. However, there are many alternative arrangements not specifically described herein, but with which the present invention is applicable. Although specific features have been provided, the compositions and methods of the present invention would equally be embodied by other configurations not specifically recited herein. The scope of the present invention should therefore not be limited by the embodiments illustrated, but rather it should be understood that the present invention has wide applicability with respect to catheter systems generally. All modifications, variations, or equivalent elements and implementations that are within the scope of the appended claims should therefore be considered within the scope of the invention.

It is understood that the foregoing detailed description and accompanying examples are merely illustrative, and are not to be taken as limitations upon the scope of the invention. Various changes and modifications to the disclosed embodiments will be apparent to those skilled in the art. U.S. patents and publications referenced herein are incorporated by reference.

What is claimed as new and desired to be protected by Letters Patent of the United States is:

1. A method of coating a vascular stent, comprising contacting a metal surface of a vascular stent with a filtered solution, the filtered solution comprising an amorphous fluoropolymer and a fluorinated organic solvent, contacting of the metal surface with the filtered solution providing a coating having a thickness in the range of about 1 micron to about 100 microns, wherein said amorphous fluoropolymer comprises tetrafluoroethylene (TEF) and 4,5-difluoro-2,2-bis(trifluoromethyl)-1,3-dioxole and includes a radio-opaque agent.

2. The method of claim 1, wherein said solution is homogenous.

3. The method of claim 1, comprising dipping or spraying said stent with said solution to provide a coated stent.

4. The method of claim 3, further comprising drying said dipped or spray-coated stent.

5. The method of claim 1, wherein said solution further comprises a therapeutic agent.

6. The method of claim 5, wherein said therapeutic agent is an anti-restenotic agent, an anti-stenotic agent, an antiproliferative agent, an immunomodulator, an antithrombotic, an antioxidant, estrogen, a growth factor inhibitor, an antisense oligonucleotide, or a collagen inhibitor.

7. The method of claim 6, wherein said therapeutic agent is paclitaxel.

8. The method of claim 1, further comprising contacting the metal surface of said stent with said solution modified by addition of the radio-opaque agent to provide a stent having a first coating, and contacting the stent having a first coating with a solution having no radio-opaque agent.

9. The method of claim 1, wherein said radio-opaque agent is barium sulfate, gold, tantalum, triiodobenzoic acid, or a triiodobenzoic acid derivative.

10. The method of claim 1, further comprising contacting the metal surface of said stent with said solution modified by addition of a salt or a compound capable of releasing a gas to provide a coated stent, and contacting said coated stent in an aqueous medium to obtain a porous amorphous fluoropolymer coating.

11. The method of claim 10, wherein said salt is an alkali metal salt.

12. The method of claim 10, wherein said compound is capable of releasing carbon dioxide upon decomposition.

13. The method of claim 12, wherein said compound comprises an isocyanate moiety.

14. The method of claim 1, wherein said amorphous fluoropolymer coating comprises tetrafluoroethylene (TEF) and from 60 mole % to 90 mole % of 4,5-difluoro-2,2-bis(trifluoromethyl)-1,3-dioxole.

15. The method of claim 1, wherein said metal is stainless steel, titanium, nickel, a metal alloy, platinum, gold, or a biocompatible metal.

16. The method of claim 15, wherein said metal is a titanium and nickel alloy.

17. The method of claim 1, wherein said coating is optically transparent or chemically resistant.

18. The method of claim 1, wherein said coating has a thickness from 1 to 20 microns.

19. The method of claim 18, wherein said coating has a thickness from 5 to 15 microns.

20. The method of claim 1, wherein said solution comprises from 0.1% to 30% by weight of said amorphous fluoropolymer.

21. The method of claim 20, wherein said solution comprises from 1% to 10% by weight of said amorphous fluoropolymer.

22. The method of claim 21, wherein said solution comprises 5% by weight of said amorphous fluoropolymer.

23. The method of claim 22, wherein said solution further comprises 5% by weight of a therapeutic agent.

24. The method of claim 23, wherein said therapeutic agent is paclitaxel.

25. The device of claim 1, wherein the coating has a coefficient friction between 0.01 and 0.4.

26. The method of claim 1, wherein the coating has a coefficient friction between 0.01 and 0.4.

* * * * *